United States Patent
Zhu et al.

(10) Patent No.: US 8,000,509 B2
(45) Date of Patent: Aug. 16, 2011

(54) IMAGE PROCESSING METHOD FOR A MICROSCOPE SYSTEM

(75) Inventors: Yanning Zhu, Hamden, CT (US); Triantafyllos Tafas, Rocky Hill, CT (US); Youngmin Kim, Wallingford, CT (US); Xiuzhong Wang, Hamden, CT (US)

(73) Assignee: IKONISYS, Inc., New Haven, CT (US)

( * ) Notice: Subject to any disclaimer, the term of this patent is extended or adjusted under 35 U.S.C. 154(b) by 935 days.

(21) Appl. No.: 11/833,204

(22) Filed: Aug. 2, 2007

(65) Prior Publication Data

US 2008/0212865 A1 Sep. 4, 2008

Related U.S. Application Data

(60) Provisional application No. 60/821,536, filed on Aug. 4, 2006.

(51) Int. Cl.
*G06K 9/00* (2006.01)
(52) U.S. Cl. ......... 382/128; 382/131; 382/132; 382/133
(58) Field of Classification Search .................. 382/128, 382/131, 132, 133
See application file for complete search history.

(56) References Cited

U.S. PATENT DOCUMENTS

| 5,225,326 | A | 7/1993 | Bresser et al. |
| 5,707,801 | A | 1/1998 | Bresser et al. |
| 6,221,607 | B1 | 4/2001 | Tsipouras et al. |
| 7,180,661 | B2 * | 2/2007 | Sasaki ........................... 359/385 |
| 2005/0002552 | A1 * | 1/2005 | Dunn et al. ................... 382/133 |

FOREIGN PATENT DOCUMENTS

WO WO 94/02646 2/1994

OTHER PUBLICATIONS

Du Manoir et al., Human Genetics 90(6): 590-610 (1993).
Harrison's Principles of Internal Medicine, 12th edition, ed. Wilson et al., McGraw Hill, N.Y., N.Y., pp. 24-46 (1991).
AneuVysion® Multicolor DNA Probe Kit sold by the Vysis division of Abbott Laboratories.
UroVysion® kit by the Vysis division of Abbott Laboratories.
U.S. Appl. No. 07/668,751.

* cited by examiner

*Primary Examiner* — Tom Y Lu
(74) *Attorney, Agent, or Firm* — Kelley, Drye & Warren LLP

(57) ABSTRACT

An embodiment is disclosed for performing the image processing for analyzing the results of a fluorescence in situ hybridization (FISH) microscopic automated sample analysis to determine specific chromosomal characteristics.

7 Claims, 6 Drawing Sheets

IMAGE PROCESSING METHOD FOR A MICROSCOPE SYSTEM

This application claims priority from U.S. Provisional Application Ser. No. 60/821,536 filed Aug. 4, 2006. All references cited in this specification, and their references, are incorporated by reference herein where appropriate for teachings of additional or alternative details, features, and/or technical background.

BACKGROUND OF THE INVENTION

1. Field of the Invention

The present invention generally relates to image processing methods employed for performing automated microscopic analysis for fluorescence in situ hybridization (FISH) detection of genetic characteristics.

2. Description of the Related Art

Conventional optical microscopy generally employs a microscope slide to which the normal human complement of chromosomes consists of the sex chromosomes (designated X and Y) and 22 autosomes (numbered 1-22). It has been estimated that a minimum of 1 in 10 human conceptions has a chromosome abnormality. As a general rule, an abnormal number of sex chromosomes is not lethal, although infertility can result. In contrast, an abnormal number of autosomes typically results in early death. Of the three autosomal trisomies found in live-born babies (trisomy 21, 18 and 13), only individuals with trisomy 21 (more commonly known as Down syndrome), survive past infancy.

Although Down syndrome is easily diagnosed after birth, prenatal diagnosis is problematic. To date, karyotyping of fetal cells remains the established method for the diagnosis of Down syndrome and other genetic abnormalities associated with an aberration in chromosomal number and/or arrangement. Such genetic abnormalities include, for example, chromosomal additions, deletions, amplifications, translocations and rearrangements. The assessment of such abnormalities is made with respect to the chromosomes of a healthy individual, i.e., an individual having the above-described normal complement and arrangement of human chromosomes.

Genetic abnormalities include the above-noted trisomies, such as Down syndrome, as well as monosomies and disomies. Genetic abnormalities also include additions and/or deletions of whole chromosomes and/or chromosome segments. Alterations such as these have been reported to be present in many malignant tumors. Thus, aberrations in chromosome number and/or distribution (e.g., rearrangements, translocations) represent a major cause of mental retardation and malformation syndromes (du Manoir et al., et al., Human Genetics 90(6): 590-610 (1993)) and possibly, oncogenesis. See also, e.g., (Harrison's Principles of Internal Medicine, 12th edition, ed. Wilson et al., McGraw Hill, N.Y., N.Y., pp. 24-46 (1991)), for a partial list of human genetic diseases that have been mapped to specific chromosomes, and in particular, for a list of X chromosome linked disorders. In view of the growing number of genetic disorders associated with chromosomal aberrations, various attempts have been reported in connection with developing simple, accurate, automated assays for genetic abnormality assessment.

In general, karyotyping is used to diagnose genetic abnormalities that are based upon additions, deletions, amplifications, translocations and rearrangements of an individual's nucleic acid. The "karyotype" refers to the number and structure of the chromosomes of an individual. Typically, the individual's karyotype is obtained by, for example, culturing the individual's peripheral blood lymphocytes until active cell proliferation occurs, preparing single, proliferating (e.g. metaphase, and possibly interphase) cells for chromosome visualization, fixing the cells to a solid support and subjecting the fixed cells to in situ hybridization to specifically visualize discrete portions of the individual's chromosomes.

The sample contains at least one target nucleic acid, the distribution of which is indicative of the genetic abnormality. By "distribution", it is meant the presence, absence, relative amount and/or relative location in one or more nucleic acids (e.g., chromosomes) known to include the target nucleic acid. In a particularly preferred embodiment, the target nucleic acid is indicative of a trisomy 21 and thus, the method is useful for diagnosing Down syndrome. In a particularly preferred embodiment, the sample intended for Down syndrome analysis is derived from maternal peripheral blood. More particularly, lymphocytes are isolated from peripheral blood according to standard procedures, the cells are attached to a solid support (e.g., by centrifuging onto glass slides), and fixed thereto according to standard procedures (see, e.g., the Examples) to permit detection of the target nucleic acid.

Nucleic acid hybridization techniques are based upon the ability of a single stranded oligonucleotide probe to base-pair, i.e., hybridize, with a complementary nucleic acid strand. Fluorescence in situ hybridization ("FISH") techniques, in which the nucleic acid probes are labeled with a fluorophore (i.e., a fluorescent tag or label that fluoresces when excited with light of a particular wavelength), represents a powerful tool for the analysis of numerical, as well as structural aberrations chromosomal aberrations. The method involves contacting a fixed cell with an antibody labeled with a first fluorophore for phenotyping the cell via histochemical staining, followed by contacting the fixed cell with a DNA probe labeled with a second fluorophore for genotyping the cell. The first and second fluorophores fluoresce at different wavelengths from one another, thereby allowing the phenotypic and genetic analysis on the identical fixed sample.

Fluorescence in situ hybridization refers to a nucleic acid hybridization technique which employs a fluorophore-labeled probe to specifically hybridize to and thereby, facilitate visualization of, a target nucleic acid. Such methods are well known to those of ordinary skill in the art and are disclosed, for example, in U.S. Pat. No. 5,225,326; U.S. patent application Ser. No. 07/668,751; PCT WO 94/02646, the entire contents of which are incorporated herein by reference. In general, in situ hybridization is useful for determining the distribution of a nucleic acid in a nucleic acid-containing sample such as is contained in, for example, tissues at the single cell level. Such techniques have been used for karyotyping applications, as well as for detecting the presence, absence and/or arrangement of specific genes contained in a cell. However, for karyotyping, the cells in the sample typically are allowed to proliferate until metaphase (or interphase) to obtain a "metaphase-spread" prior to attaching the cells to a solid support for performance of the in situ hybridization reaction.

Briefly, fluorescence in situ hybridization involves fixing the sample to a solid support and preserving the structural integrity of the components contained therein by contacting the sample with a medium containing at least a precipitating agent and/or a cross-linking agent. Exemplary agents useful for "fixing" the sample are well known to those of ordinary skill in the art and are described, for example, in the above-noted patents and/or patent publications.

One fluorescent dye used in fluoresence microscopy is DAPI or 4',6-diamidino-2-phenylindole [CAS number: [28718-90-3], a fluorescent stain that binds strongly to DNA. Since DAPI will pass through an intact cell membrane, it may be used to stain live and fixed cells. DAPI is excited with ultraviolet light. When bound to double-stranded DNA its absorption maximum may be about 358 nm and its emission maximum may be about 461 nm. DAPI will also bind to RNA, though it is not as strongly fluorescent. Its emission shifts to about 400 nm when bound to RNA. DAPI's blue emission is convenient for microscopists who wish to use multiple fluorescent stains in a single sample. There is very little fluorescence overlap, for example, between DAPI and green-fluorescent molecules like fluorescein and green fluorescent protein (GFP), or red-fluorescent stains like Texas Red. Other fluorescent dyes are used to detect other biological structures.

Other types of fluorescing materials are used in fluorescence in situ hybridization (FISH). The FISH method uses fluorescent tags to detect chromosomal structure. Such tags may directed to specific chromosomes and specific chromosome regions. Such technique may be used for identifying chromosomal abnormalities and gene mapping. For example, a FISH probe to chromosome 21 permits one to identify cells with trisomy 21, i.e., cells with an extra chromosome 21, the cause of Down syndrome. FISH kits comprising multicolor DNA probes are commercially available. For example, Aneu-Vysion® Multicolor DNA Probe Kit sold by the Vysis division of Abbott Laboratories, is designed for in vitro diagnostic testing for abnormalities of chromosomes 13, 18, 21, X and Y in amniotic fluid samples via fluorescence in situ hybridization (FISH) in metaphase cells and interphase nuclei. The AneuVysion® Assay (CEP 18, X, Y-alpha satellite, LSI 13 and 21) Multi-color Probe Panel uses CEP 18/X/Y probe to detect alpha satellite sequences in the centromere regions of chromosomes 18, X and Y and LSI 13/21 probe to detect the 13q14 region and the 21q22.13 to 21q22.2 region. The AneuVysion kit is useful for identifying and enumerating chromosomes 13, 18, 21, X and Y via fluorescence in situ hybridization in metaphase cells and interphase nuclei obtained from amniotic fluid in subjects with presumed high risk pregnancies. The combination of colors emitted by the tags is used to determine whether there is a normal chromosome numbers or trisomy.

In a similar vein, the UroVysion® kit by the Vysis division of Abbott Laboratories designed to detect chromosomal abnormalities associated with the development and progression of bladder cancer by detecting aneuploidy for chromosomes 3, 7, 17, and loss of the 9p21 locus via fluorescence in situ hybridization in urine specimens from persons with hematuria suspected of having bladder cancer. The UroVysion Kit consists of a four-color, four-probe mixture of DNA probe sequences homologous to specific regions on chromosomes 3, 7, 9, and 17. The UroVysion probe mixture consists of Chromosome Enumeration Probe (CEP) CEP 3 Spectrum-Red, CEP 7 SpectrumGreen, CEP 17 SpectrumAqua and Locus Specific Identifier (LSI 9p21) SpectrumGold.

Despite the above-described advances in the development of fluorescent in situ hybridization methods for the diagnosis of genetic abnormalities, the analysis of the fluorophore-labeled sample remains labor-intensive and involves a significant level of subjectivity. This is particularly true in connection with the prenatal diagnosis of genetic abnormalities in which fetal cells must either be isolated from maternal cells or visually distinguished therefrom prior to assessment for genetic abnormalities. Thus, for example, a laboratory technician must manually prepare and sequentially stain the sample (first, with a histochemical stain to phenotype the cells, second, with a hybridization probe to genotype the cell); visually select fetal cells from other cells in the optical field (using, for example, the above-mentioned histochemical staining procedure); assess the relative distribution of fluorescent color that is attributable to hybridization of the fluorophore-tagged probe; and compare the visually-perceived distribution to that observed in control samples containing a normal human chromosome complement. As will be readily apparent, the above-described procedure is quite time-consuming. Moreover, because the results are visually-perceived, the frequency of erroneous results can vary from one experiment to the next, as well as from one observer to the next.

The invention disclosed in co-owned U.S. Pat. No. 6,221,607, "Automated fluorescence in situ hybridization detection of genetic abnormalities," discloses computer-implemented methods for determining a genetic abnormality such as trisomy 21 which eliminate subjective analysis of selectively stained chromosomes. More specifically, the patent provides a method for detecting whether a genetic abnormality is present in a fixed sample containing at least one target nucleic acid. The method is useful for diagnosing genetic abnormalities associated with an aberration in chromosomal number and/or arrangement, such as, for example, chromosomal additions, deletions, amplifications, translocations and rearrangements.

SUMMARY OF THE INVENTION

Embodiments are disclosed which perform various image processing functions which may be employed to implement the automated fluorescence in situ hybridization method. The embodiments include an auto-exposure method for acceptably imaging all regions of the sample over an intensity range exceeding the dynamic range of the digital electronies; a method for fluorescence in situ hybridization (FISH) object of interest enumeration which locates targets within the sample; nuclei identification which is a method for classifying and characterizing the objects-of-interest enumerated; segmenting nuclei which, is a method for defining the shape of an identified object of interest. Embodiments of the method are useful to characterize cell nuclei, or to enumerate a chromosome. An embodiment of the method is adapted for conducting an AneuVysion™ assay (Vysis, Inc., Downers Grove, Ill.).

In an embodiment, there is disclosed:

An image processing method for analyzing a fluorescence in situ hybridization image of a fluorescently-hybridized specimen using a microscope system having a fluorescence exciting light source and an electronic imaging device, the method comprising the steps of:

illuminating the specimen with fluorescence exciting illumination;

adjusting exposure parameters of the electronic imaging device for capturing an image of the specimen at a depth of focus within an illuminated field;

enumerating objects of interest in a captured image of the specimen;

identifying a nucleus in the image;

segmenting a nucleus in the image;

counting and characterizing a fluorescent signal occurring within the nucleus; and interpreting and reporting results.

DETAILED DESCRIPTION OF THE INVENTION

Figure 1:
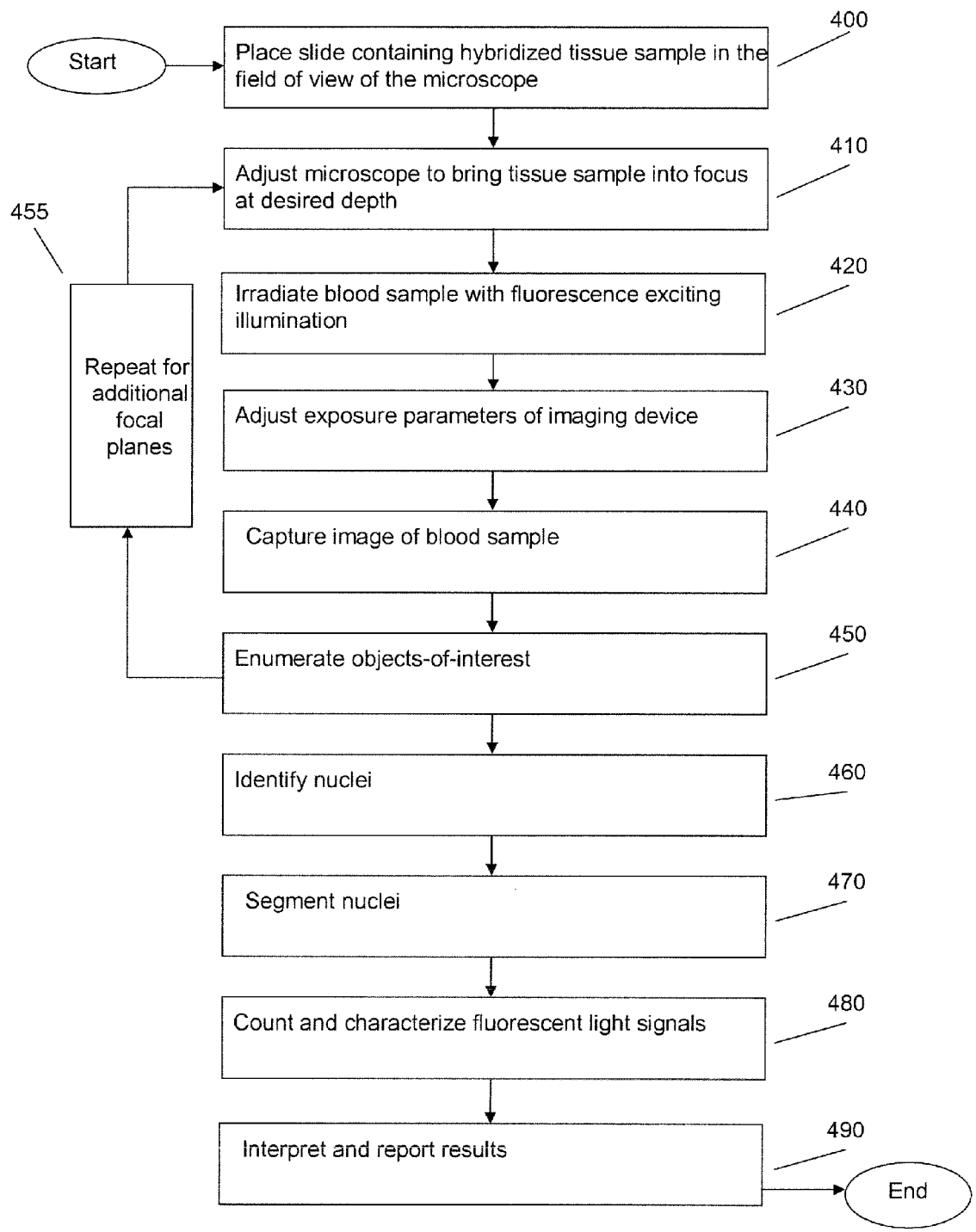
FIG. 1 is a flow chart representing an overview of an embodiment of a computer program for carrying out the automated analysis of the invention.

Auto-Exposure: The acquisition of the digital image typically requires proper exposure of all of the regions of the specimen being examined. The electronic imaging device may be a multi-pixel planar array of light-sensitive detectors in a charge coupled device (CCD), or complementary metal oxide semiconductor (CMOS) elements, or any other technology suitable for converting an optical image into electrical signals. Exemplary CCD cameras include intensified CCD cameras utilizing gating techniques to achieve gate speeds of less than about nine nanoseconds with improved quantum efficiency (e.g., such as Princeton Instruments (Trenton, N.J.) PIMAX$_{MG}$ which support a full range of 16-bit scientific-grade CCDs), allowing for a very fast response limited by the time constant of the output phosphor, and electron-bombarded CCD (EBCCD) wherein photons are detected by a photocathode and released electrons are accelerated across a gap and impact on the hack side of a CCD (allowing for additional gain and accompanying speed). CMOS cameras in particular may find use in fluorescence microscopy. CMOS cameras have an amplifier and digitizer associated with each photodiode in an integrated on-chip format. Recent CMOS sensors have a greatly reduced residual noise, and provide an extraordinary dynamic range.

Low intensity detection can be enhanced through the employment of an image intensifier and similar technologies. The correct exposure time may be calculated using an algorithm which takes into account conditions such as (i) the range of mean image intensity value within certain areas (nuclei), (ii) the range of highest image intensity, (iii) the maximum allowed exposure time, and (iv) independently provided exposure conditions.

Each sensor picture element or pixel typically accumulates an electrical charge which is in proportion to the number of photons (amount of light) falling on the element. As there is usually an inverse linear relationship between required exposure time and intensity of the light impinging on the pixel, dimmer areas may be imaged in separate exposures by increasing exposure time. After exposure, the pixels of the imaging arrays can be individually measured in a sequential scanning pattern. Each of the element measurements can then be digitized by means of an analog to digital converter (A/D) or other means of digitizing the data. The resulting stream of digitized measurements can be stored in a memory upon which image analysis procedures may be performed.

In most cases, however, a single exposure time does not adequately image all portions of the specimen since the dynamic range of the image sensor and associated electronics is typically less than the range of intensities emanating from various locations of a single specimen. For example, the dynamic range of an 8 bit D/A converter is 256:1, which may be inadequate for this application. For that situation, with a single exposure time, either bright objects or nuclei will be lost if the dimmest objects are properly exposed or, alternatively, dim objects will be lost when the brightest objects are properly exposed.

When the intensity dynamic range of the imaging field is too large for a single exposure duration, a multiple exposure strategy can be employed. The portions of the specimen or nuclei with the highest intensities are exposed first using a relatively shorter exposure time, and analyzed. For that exposure, the dimmer areas of the image may be next analyzed using edge detection or entropy measurement to determine whether a longer exposure time is necessary to adequately image those areas. If so, an additional exposure can be made for an appropriately longer exposure time, with the pixel measurements corresponding to the high intensity nuclei excluded or masked from the image. The process may be repeated, for longer exposure times, until no more structures of interest are found. As an alternative to a longer exposure time, multiple shorter exposures may be computationally combined to synthesize a single longer exposure. Alternatively, the exposure may be varied by changing the effective microscope aperture or irradiating intensity.

"Dot" Enumeration: The specimen has finite thickness with objects of interest dispersed throughout the depth of the sample. As used herein, an "object of interest" relates to any feature in a microscope field that has been identified as a result of labeling with a FISH probe. Nonlimiting examples of an object of interest include the plasma membrane or portion thereof, a cytoplasmic organelle or structure, a ribosome, a mitochondrion or portion thereof, a mitochondrial nucleic acid, a Golgi membrane, endoplasmic reticulum or portion thereof, an endosome, a nucleus, a nucleolus, a nuclear membrane or portion thereof, a chromosome or portion thereof, and a portion of a DNA molecule. Imaging, therefore, requires that the optical system be individually focused to form well resolved images of each of the objects. Alternatively, a series of exposures may be taken at spaced focal planes selected at sufficiently small intervals so that all objects of interest are acceptably focused. The required number and separation of the focal planes can readily be determined from the thickness of the specimen and the depth-of-field of the optical system.

Once the properly focused exposures have been obtained, the images can be processed to identify and separate the objects of interest or fluorescence in situ hybridization "dots." These "dots" are revealed by the fluorescent light that they emit, and the properties of the emitted light vary in accordance with the characteristics of the object. In particular, nonlimiting examples of fluorescent properties emanating from an object of interest include optical properties of the fluorescent label, and the intensity of hybridization of the FISH probe to the object.

Having obtained the images, an enumeration algorithm may be employed to enumerate the fluorescence in situ hybridization objects of interest ("dots"). The first step of the algorithm can be segmentation of the 4',6-diamidino-2-phenylindole (DAPI, a double-stranded DNA staining fluorescent probe) stained image, in accordance with intensity, effectively defining intensity contours of brightness across each of the image focal planes. The raw fluorescence in situ hybridization channel images may be computationally converted into contrast images. Contrast images are a mathematical transformation of the original image where the intensity of each transformed pixel represents the change in intensity relative to the adjoining pixels in the original image. Objects within the nuclei may be resolved by successively lowering the contrast threshold from the highest possible value to a preset low value. For each object, the highest contrast can be compared to the moving average and standard deviation of the previous objects. If a significant jump in contrast is detected, all the objects with higher contrast can be marked as potential fluorescence in situ hybridization "dots." In addition, if two potential fluorescence in situ hybridization "dots" are positioned closer than a preset threshold value, they may be merged to form a single "dot." The relative contrasts and sizes of the identified potential fluorescence in situ hybridization "dots" can be compared, and the final fluorescence in situ hybridization "dots" can be characterized and logged in a data base.

Nuclei Identification: Once the potential objects of interest or fluorescence in situ hybridization "dots" are identified, automatic pattern recognition techniques may be employed to classify and characterize each of the objects. Each of the fluorescence in situ hybridization "dot" sites determined by the fluorescence in situ hybridization "dot" enumeration analysis can be analyzed to develop an elliptic Fourier shape descriptor of the object that is invariant to translation, rotation and scaling. Other characterizations, including but not limited to object size and emitted intensity distribution within the nucleus, may also be employed to describe the object. A pattern recognition algorithm can be employed to identify and categorize the object of interest based on these characterizations. Initially, the pattern recognition algorithm may be trained by employing an expert human observer to classify the object and input his result into the pattern recognition data base. After the initial learning period, the algorithm can be performed automatically and the pattern recognition data base continually updated.

Segmenting Nuclei: For each nucleus identified by the pattern recognition algorithm, contours of constant intensity starting at maximum brightness can be determined. At each point on the respective contour, the gradient may also be computed. The size of the nucleus can be determined, by way of nonlimiting example, as the contour corresponding to the greatest average gradient.

AneuVysion™ Scanning Method: The AneuVysion™ assay is an FDA cleared test for prenatal diagnosis which allows for rapid detection of the most common abnormalities of chromosome number using fluorescence in situ hybridization. It utilizes molecular genetic techniques to create a fluorescent DNA probe that produces a bright microscopic signal when it selectively attaches to one specific part of a particular chromosome. The DNA probes are able to attach to the appropriate chromosomes in non-dividing cells. The signals are different colors for different chromosomes. By counting the number of signals within a cell, the cytogenetic technologist knows whether either the normal number or a trisomy, monosomy or other aneusomy of the detectable chromosomes is present in the fetus.

The disclosed embodiments can be employed to effectively automate the AneuVysion™ assay utilizing the following method. A computational histogram may be organized where each bin in the histogram represents each possible combination of chromosomal constituency. The AneuVysion™ CEP (Chromosome Enumeration Probe) analysis results utilize a histogram structure including three coefficients representing the X chromosome, the Y chromosome and chromosome 18. A second histogram structure corresponding to the LSI probe includes two coefficients representing chromosome 12 and chromosome 13. The automated fluorescence microscope system finds a specified number (N) of nuclei using low magnification. In nonlimiting examples, the value of N is specified to be an integer such as 10, or 20, or 30, or 40, or 50, or 60, or 80, or 100, or 125, or 150, or 200, or even more. Furthermore, N may be specified to be an integer anywhere between the values identified herein. The system then individually images each nucleus using high magnification. The fluorescence in situ hybridization light points are counted for all channels and the results are organized into the above described histogram formulation. The measurement process continues until one bin count reaches a predetermined number (M). For example, the number M may be 50, corresponding to current government guidelines. More generally, in nonlimiting examples, the value of M is predetermined to be an integer such as 10, or 20, or 30, or 40, or 50, or 60, or 80, or 100, or 125, or 150, or 200, or even more. Furthermore, M may be predetermined to be an integer anywhere between the values identified herein. If, when the N nuclei have been measured, no bin contains the required M quantity, the system may search for additional nuclei at low magnification and continue the measurement at high magnification until one bin reaches the quantity N. When N is reached, the measurement stops and the highest bin count may be compared with the next highest bin count. If the highest bin count is some predetermined percentage greater than the next greatest, then the result corresponding to that bin can be reported as the clinical result. If it is does not satisfy the condition, then an inconclusive result can be reported. In various nonlimiting examples, the predetermined percentage for comparing the highest bin count with the next highest bin count may be 5%, or 10%, or 15%, or 20%, or 25%, or 30%, or 35%, or 40%, or 45%, or 50%, or 60%, or 70%, or 80%, or 90%, or 100%, or 125%, or 150%, or 175%, or 200%, or even a higher percent value. Furthermore, the predetermined percentage may be set at any integral or nonintegral value between those identified herein.

An embodiment of the image processing method for analyzing fluorescence in situ hybridization images of the present invention is schematically portrayed in FIG. 1. A microscope slide containing a specimen which has been suitably treated to hybridize it in situ to a fluorescent probe is placed 400 in the field of view of a microscope. In a nonlimiting embodiment the basic elements of a microscope that may be used in the present method include an X-Y stage, a mercury or equivalent light source suitable to excite fluorescence of the labels, a fluorescence microscope, a color detecting CCD image detecting device, a computer, and one or more monitors. The individual elements of the system may be custom-built or purchased off-the-shelf as standard components. Nonlimiting examples of specimens include cells, blood cells, epithelial cells, tissues, disrupted tissues, tissue slices, biopsy samples, excised surgical samples, and the like.

The microscope is adjusted 410 to bring the specimen into focus at a focal plane of choice within the depth of the specimen. The specimen is irradiated 420 with fluorescence exciting illumination causing various loci of the sample having a labeled probe bound to fluoresce. The exposure parameters of the electronic imaging device are adjusted to properly expose these areas 430. As is well known in the art, the exposure parameters may be varied by changing exposure time, and/or aperture, and/or illumination level. An image is captured 440.

Figure 2:
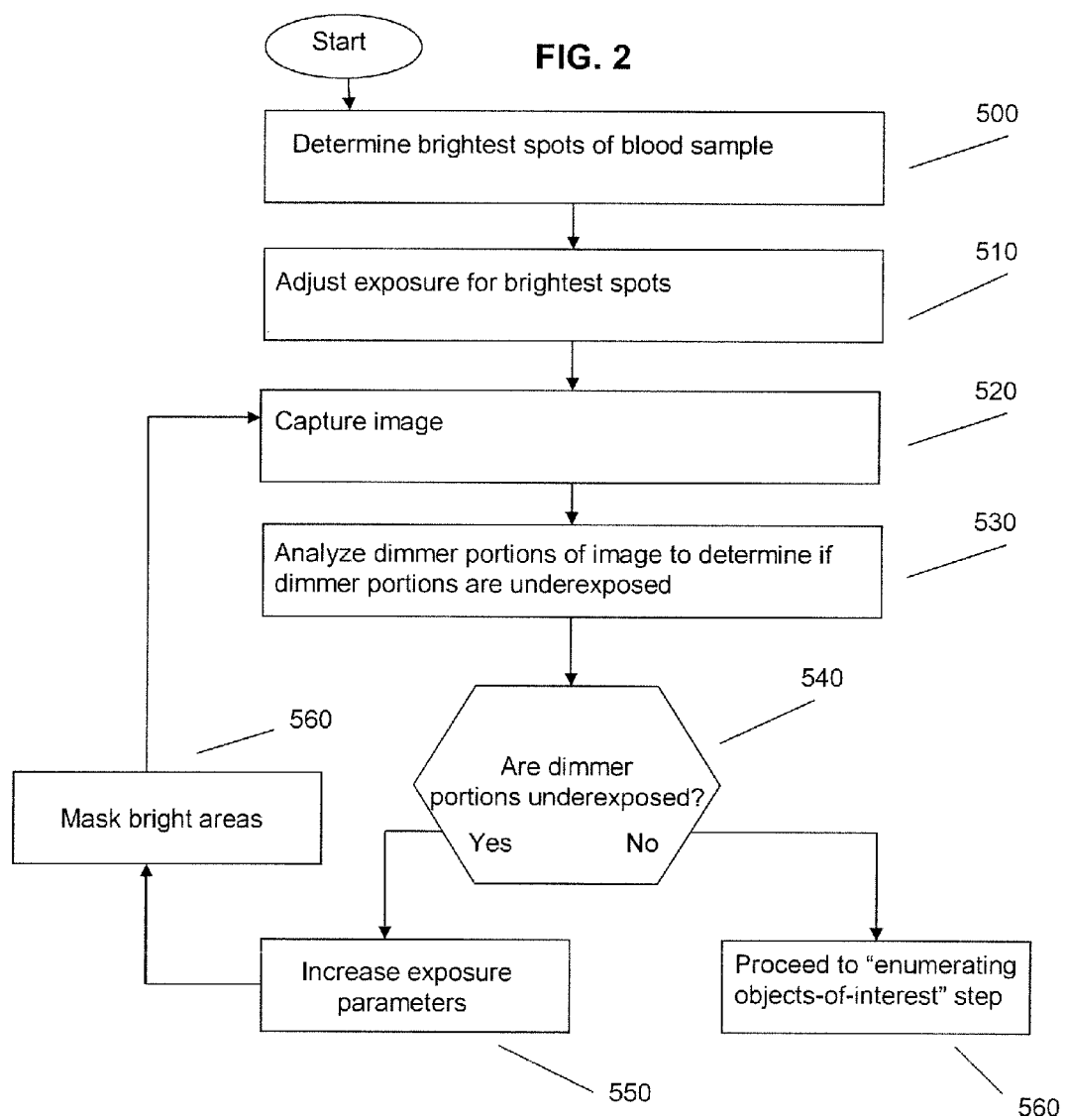
FIG. 2 is a flow chart representing an embodiment of a program module for adjusting exposure parameters.

In many cases, the intensity range in a field under scrutiny and provided in a captured image (FIG. 1, 440) will exceed the dynamic range capabilities of the electronic imaging device and/or its supporting electronics. For those situations, referring to FIG. 2, the exposure is adjusted using a sequence of images. The brightest spots are first identified 500 and the exposure parameters are set 510 so that the brightest spots are properly exposed, corresponding to the top end of the electronic imaging device's dynamic range. An image is captured 520 under these conditions. The less bright portions of the captured image are analyzed 530 to determine if detail was lost due to underexposure. Underexposure of these areas may not detect dimmer fluorescent spots. If there is a lack of detail in these dimmer regions 540, the exposure parameters are increased 550 to extend the electronic imaging device's dynamic range into the region below the initial dynamic range. The range of the electronic imaging device's supporting electronics is adjusted to correspond to the lower intensity levels to be imaged; the output of the image sensor's pixels corresponding to the initial brightest areas are masked or bypassed 560 so as not to overload the supporting electronics. A new image is captured 520 and similarly analyzed 530. This process is repeated until the entire image has been acceptably imaged 570. The objects-of-interest are next enumerated from the set of captured images (FIG. 1, 450).

Figure 3:
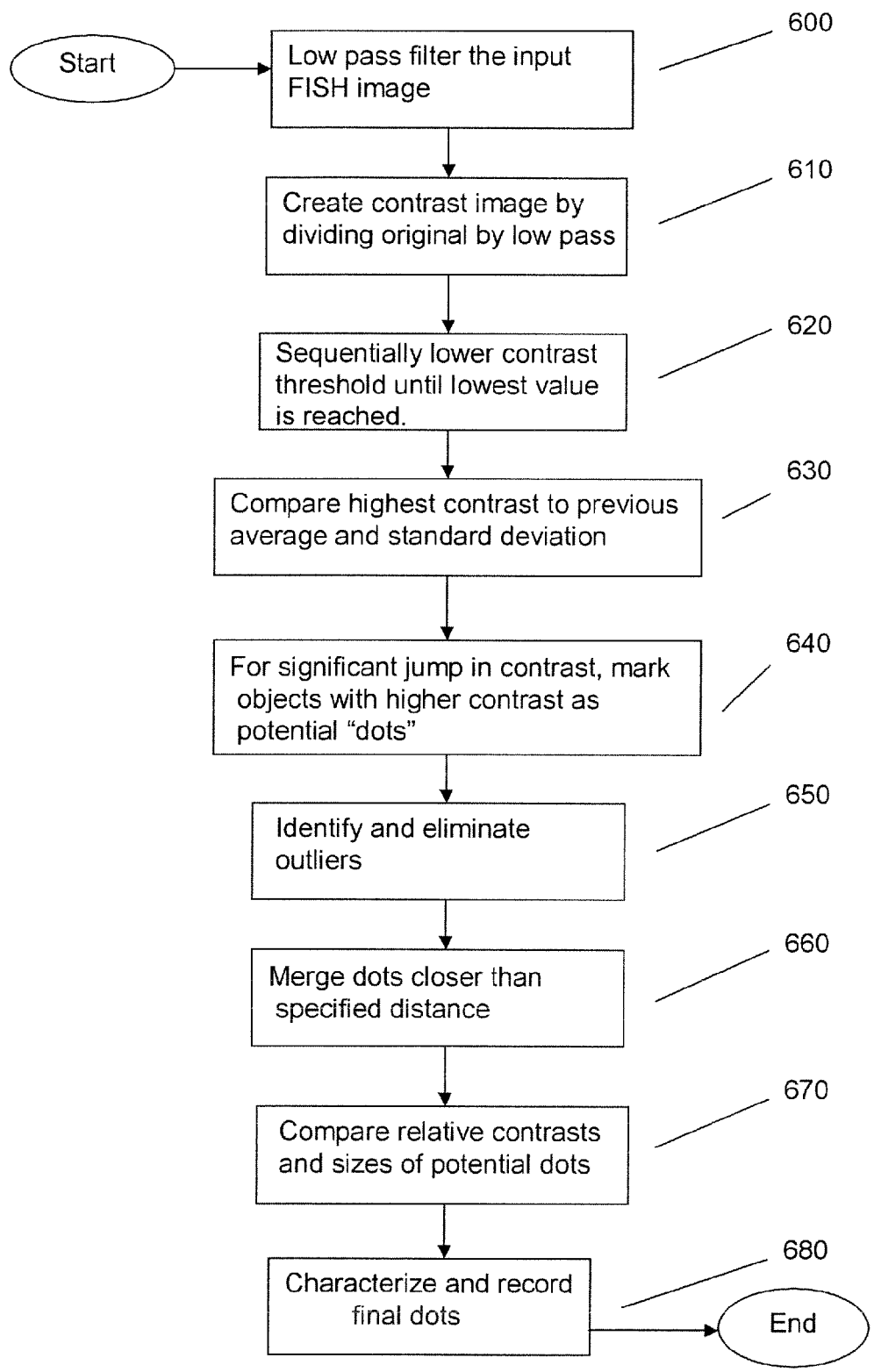
FIG. 3 is a flow chart representing an embodiment of a program module for enumerating objects of interest.

Referring to FIG. 3, a schematic presentation of an enumeration algorithm, for a given level in the depth of the field of scrutiny the captured images are low pass filtered 600. The images may be mathematically re-expressed as contrast images 610 by dividing each of the original images by the corresponding low pass filtered version. Objects-of-interest and attributes may be identified by creating contours of constant contrast. Contours of successively lower constant contrast may be resolved 620 by sequentially lowering the contrast threshold from the highest observed value to a selected low value. For each object, the highest contrast may be compared 630 to the moving average and the standard deviation of the previous objects. If a significant jump in contrast is detected 640, all the objects with higher contrast can be marked as potential objects of interest ("dots"). A "dot" is considered an outlier 650 if it has significantly lower contrast or lesser size and is excluded from further consideration. In addition, if two potential fluorescence in situ hybridization "dots" are positioned closer than a preset threshold value, they may be merged 660 to form a single "dot." The relative contrasts and sizes of the identified potential fluorescence in situ hybridization "dots" can be compared, 670 and the final fluorescence in situ hybridization "dots" can be characterized and logged in a data base 680. The process is repeated (FIG. 1, 455) for additional planes of focus required to perform the analysis throughout the depth of the sample.

Figure 4:
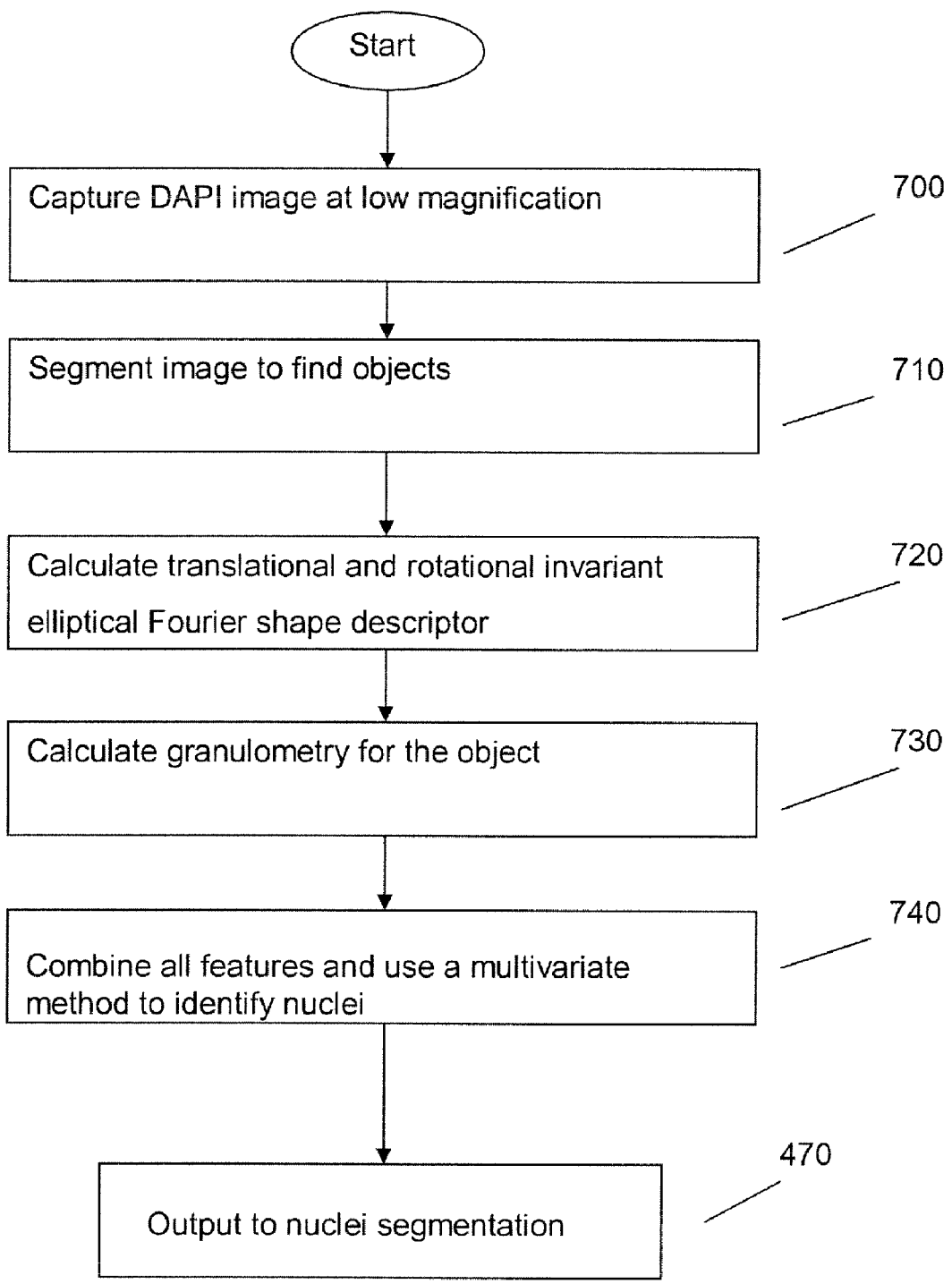
FIG. 4 is a flow chart representing an embodiment of a program module for identifying nuclei.

Having enumerated the objects-of-interest, the nuclei are then identified (FIG. 1, 460). As schematically shown in FIG. 4, a properly focused and exposed DAPI image is acquired at low magnification 700. Contours of constant intensity are mathematically generated to segment the image, thereby identifying the objects 710. For each of the objects enumerated 450, a shape characterization such as an elliptic Fourier shape descriptor that is invariant to translation, rotation and scaling is computed 720. The granulometry, or size distribution, of the constituent features of each object is computed 730. The combination of all of the variables used to classify the object and characterizations is employed to fully describe the nuclei. A pattern recognition algorithm, in conjunction with an experience based pattern data base, is used to identify and categorize the object-of-interest 740.

Figure 5:
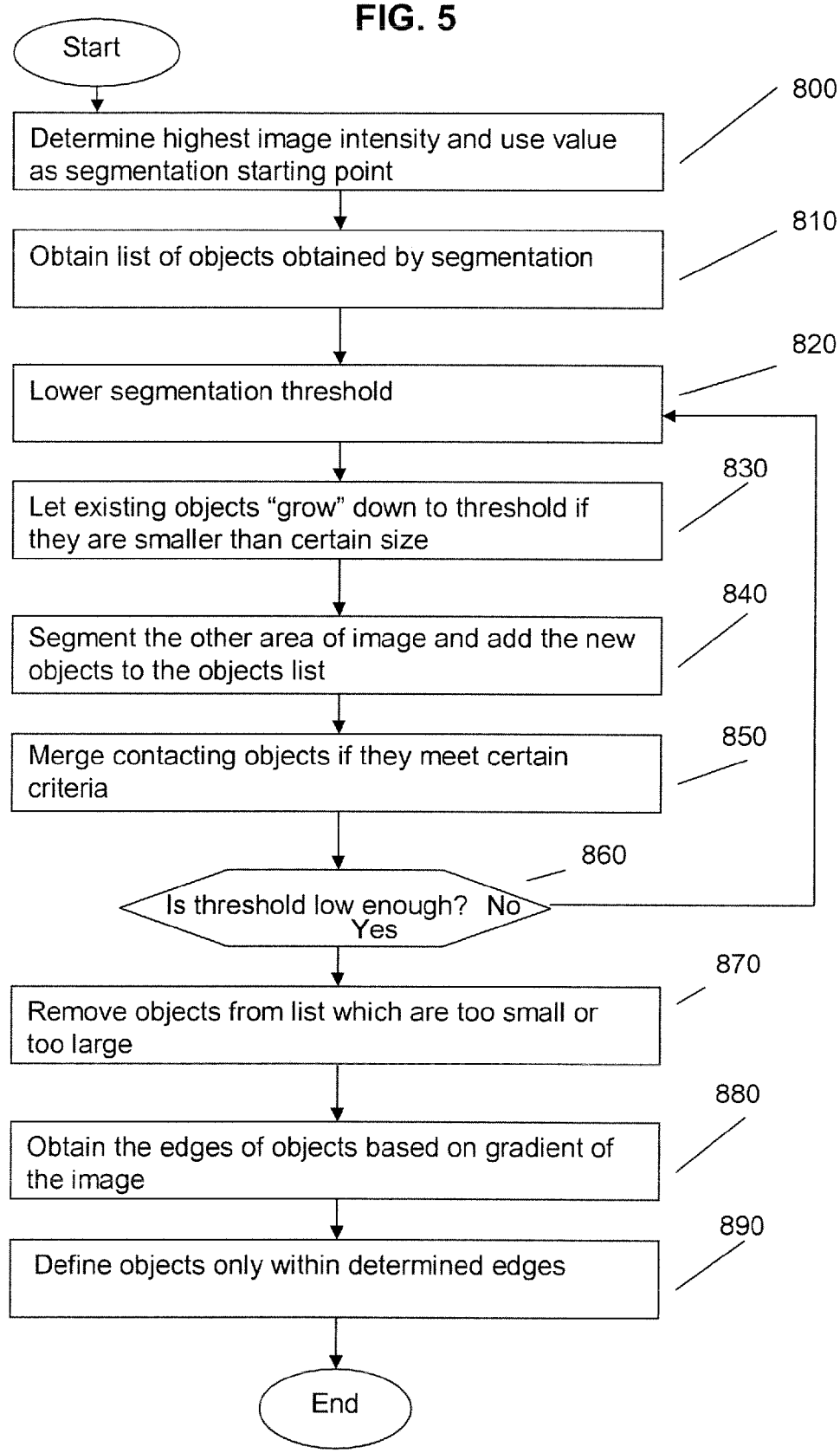
FIG. 5 is a flow chart representing an embodiment of a program module for segmenting nuclei.

The nuclei thus identified are next segmented (FIG. 1, 470) as schematically shown in FIG. 5. A contour of constant intensity, corresponding to the highest intensity, is first computed 800. The characteristics of the objects thereby identified are recorded 810. The threshold intensity level is successively reduced and new contours are computed 820. As the intensity threshold is lowered, the contour associated with each of the objects will expand 830, and new objects may become visible 840. In some cases, objects which are separated at higher intensity levels may merge as the threshold is reduced 850. The computation of additional contours is terminated once the intensity threshold level has reached a sufficiently low level 860. A threshold level determination generally uses instrumental or system parameters that are particular to the microscope system being used. Thus establishing a threshold is a procedure particular to the installation.

By way of nonlimiting example, a microscope system may provide intensity measurements as photon counts, or current, or charge accumulation. A worker of skill in the field of the invention understands and can implement evaluations of threshold levels that distinguish from overall background, on the one hand, and significant contour intensity levels on the other. At that point, objects which do not conform to the valid size range may be eliminated from further consideration 870. The contours of constant brightness which have already been computed are used to determine the edges of each of the objects 880. At each point along each contour, the intensity gradient is computed and averaged. The boundary of each nucleus is defined as the contour having the greatest average gradient. The objects are thenceforth defined only within their edges 890.

Figure 6:
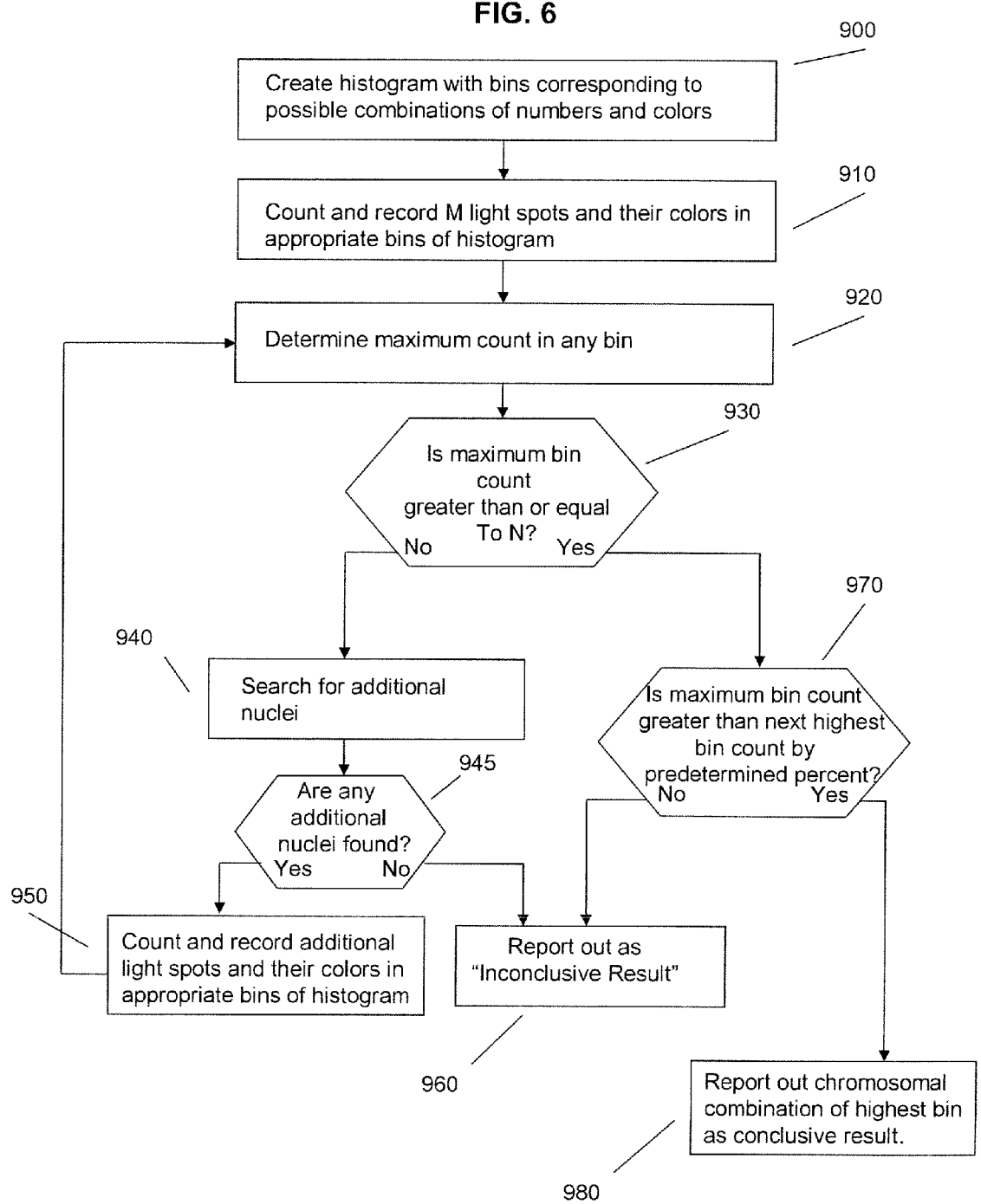
FIG. 6 is a flow chart representing an embodiment of a program module for characterizing signals and reporting results.

Having thus defined and segmented the nuclei (FIG. 1, 470), the fluorescent light signals within each nucleus are counted and characterized (FIG. 1, 480), then interpreted and the results reported (FIG. 1, 490). An embodiment of this final step is shown in FIG. 6 and is suitable for use, for example, with an AneuVysion™ assay. As previously described, the AneuVysion™ assay is a test for prenatal diagnosis. The disclosed embodiment described in this application is equally valid for other fluorescence in situ hybridization assays. A mathematical histogram structure is created 900 so that each bin corresponds to a possible combination of fluorescent light spot quantities and colors contained in a nucleus. Each of the first group of N fluorescent light spots is counted 910, its color is characterized, and the results are added to the appropriate bin of the histogram. After the first N spots have been counted, the maximum count in any of the histogram bins is determined 920. If that maximum is less than N 930, additional nuclei are located 940. Nonlimiting examples for values of N have been disclosed above. If no new nuclei can be located 945, an inconclusive result is reported. The number M is predetermined and may correspond to regulatory requirements. A exemplary value for M is 50. Nonlimiting examples for values of M have been disclosed above. The associated additional light spots are counted and characterized 950, and the results are added to the existing bin contents. This process continues until the maximum bin count is greater than or equal to N 930. When the maximum number in any bin has reached M, the number in the next greatest histogram bin is determined 970. If M exceeds the next greatest number by a predetermined Z percent, the chromosomal constituency is reported out 980 as a valid test result. Nonlimiting examples for values of a predetermined percent have been disclosed above. If, on the other hand, M does not exceed the next greatest number by Z percent, the test is reported out as inconclusive 960.

STATEMENT REGARDING PREFERRED EMBODIMENTS

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

What is claimed is:
1. An automated microscope method comprising:
    illuminating a specimen that has been hybridized with a fluorescent label;

capturing one or more images of said specimen with an electronic imaging device having a dynamic intensity range wherein said capturing comprises performing steps a) through e), one or more times, until dimmest portions of said specimen are exposed above a minimum end of said dynamic intensity range:
  a) determining brightest spots of said specimen;
  b) adjusting exposure parameters so that said brightest spots are exposed at a maximum end of said dynamic intensity range;
  c) capturing an image using said electronic imaging device;
  d) analyzing dimmest portions of said captured image to determine if said dimmest portions are exposed above said minimum end of said dynamic intensity range;
  e) if said dimmest portions of said image are not exposed above said minimum end of said dynamic intensity range, masking said brightest spots, and increasing said exposure parameters for next image;
enumerating objects of interest in said one or more captured images;
identifying and segmenting at least one nucleus within said specimen in said one or more captured images;
counting, characterizing, and reporting at least one fluorescent signal emitted by said fluorescent label within said nucleus.

2. The method of claim 1, wherein enumerating objects-of-interest further comprises:
  capturing multiple images at focal planes spaced across the depth of said hybridized specimen;
  computationally transforming said captured images into contrast images characterized by contours of constant contrast; and
  performing an enumeration algorithm to enumerate said objects-of-interest throughout the depth of said hybridized specimen.

3. The method of claim 1, wherein identifying at least one nucleus further comprises:
  a) computing a translation, rotation and scaling invariant shape descriptor of each object of interest
  b) computing a size distribution of each object of interest; and
  c) employing a pattern recognition algorithm, in conjunction with an experience based pattern data base, to identify and categorize said object-of-interest.

4. The method of claim 1, wherein segmenting at least one nucleus further comprises:
  a) computing contours of constant brightness at successive intensity intervals beginning at a local maximum and proceeding toward a low threshold level of intensity;
  b) computing an average gradient for each said contour; and
  c) defining a boundary of each said nuclei as the contour having the greatest said average gradient for said nucleus.

5. The method of claim 1, wherein counting, characterizing, and reporting at least one fluorescent signal further comprises:
  a) creating a mathematical histogram structure so that each bin corresponds to a possible combination of said spot quantities and colors contained in a nucleus;
  b) counting each of the fluorescent light spots and characterizing their respective colors;
  c) recording the results of said counting in the appropriate said bins of said histogram;
  d) continuing said count until said count in one said bin corresponds to a predetermined number;
  e) stopping said count and comparing the count in said bin to the second largest count in any other bin;
  f) reporting a maximum number bin identifier if said second largest number is less than a predetermined percentage of said predetermined number; or, alternatively,
  g) reporting inconclusive results if said second largest number is equal to or greater than a predetermined percentage of said predetermined number.

6. The method of claim 1 wherein a cell nucleus is characterized.

7. The method of claim 1 wherein a chromosome is enumerated.

* * * * *